United States Patent [19]

Ray et al.

[11] Patent Number: 5,026,373
[45] Date of Patent: Jun. 25, 1991

[54] SURGICAL METHOD AND APPARATUS FOR FUSING ADJACENT BONE STRUCTURES

[75] Inventors: Charles D. Ray, Deephaven; Eugene A. Dickhudt, New Brighton, both of Minn.

[73] Assignee: Surgical Dynamics, Inc., Alameda, Calif.

[21] Appl. No.: 432,088

[22] Filed: Nov. 6, 1989

Related U.S. Application Data

[62] Division of Ser. No. 259,031, Oct. 17, 1988, Pat. No. 4,961,760.

[51] Int. Cl.⁵ .............................................. A61F 1/03
[52] U.S. Cl. .................................. 606/61; 606/86; 623/16; 623/18
[58] Field of Search ................. 606/61, 86; 623/16-22

[56] References Cited

U.S. PATENT DOCUMENTS

| | | | |
|---|---|---|---|
| Re. 31,865 | 4/1985 | Roux | 623/18 |
| 3,720,959 | 3/1973 | Hahn | 623/16 |
| 4,492,226 | 1/1985 | Belykh | 606/61 |
| 4,501,269 | 2/1985 | Bagby | 606/61 X |
| 4,522,200 | 6/1985 | Stednitz | 606/61 X |
| 4,599,086 | 7/1986 | Doty | 606/61 |
| 4,677,972 | 7/1987 | Tornier | 606/61 |
| 4,834,257 | 5/1989 | Brantigan | 606/61 X |
| 4,961,740 | 9/1990 | Ray et al. | 606/61 |

FOREIGN PATENT DOCUMENTS 7442974 7/1976 France .

*Primary Examiner*—Robert A. Hafer
*Assistant Examiner*—Kerry Owens
*Attorney, Agent, or Firm*—Fleisler, Dubb, Meyer & Lovejoy

[57] ABSTRACT

A fusion cage 10 having an external thread 12 can be surgically inserted into a threaded bore extending laterally between the adjacent bony structures such as two vertebrae 94, 95 with the thread 12 penetrating into cancellous bone of each of the vertebrae 94, 95. The fusion cage 10 is easily screwed into place by hand without damage to the bony structures 94, 95. Cage 10 is then packed with a bone-growth-inducing substance such as cancellous bone. When a pair of such cages 10 are implanted between adjacent vertebrae 94, 95, patients have been able to sit without pain by the second or third day, much earlier than has been possible in prior spinal fusions except those involving steel plates and screws. Eventually, the ingrowth of bone through perforations 13 in the valley 14 of the thread 12 of the fusion cage 10 forms a permanent interconnection between the two bony structures 94, 95.

12 Claims, 4 Drawing Sheets

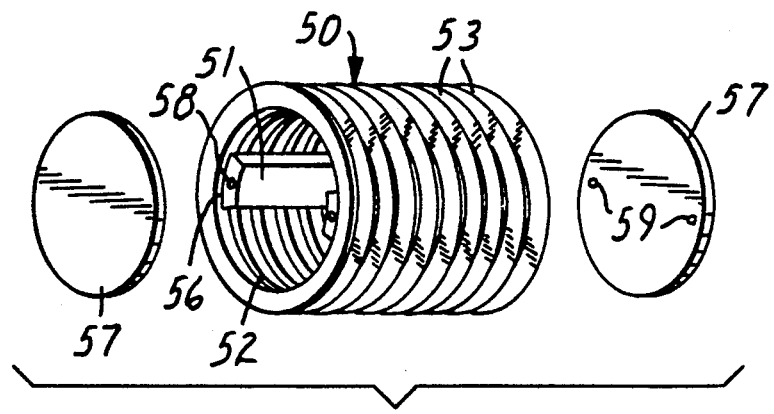
FIG.5
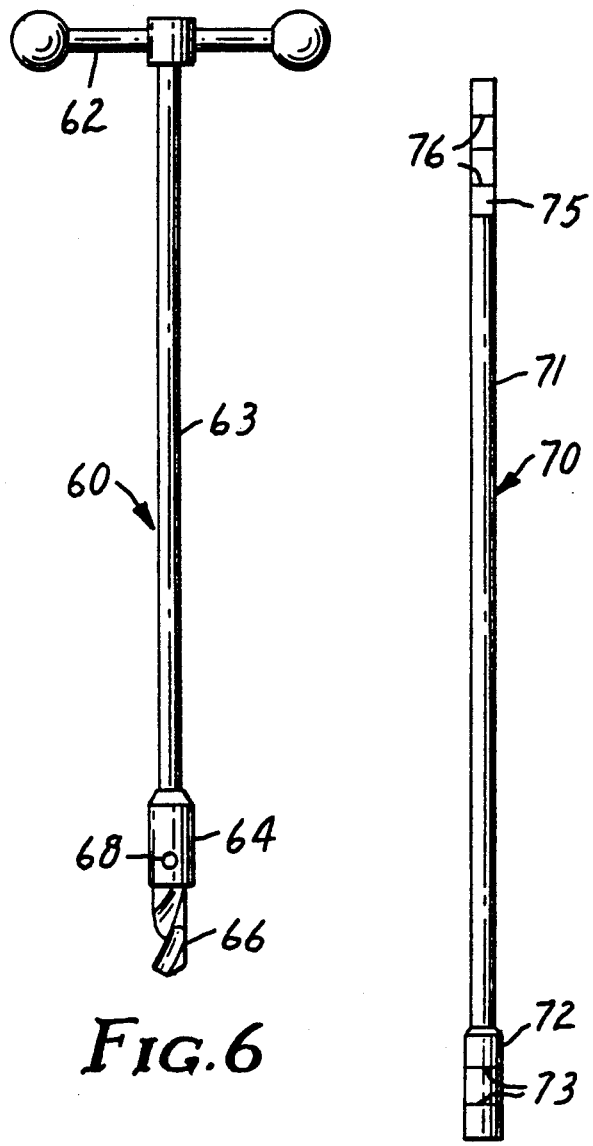
FIG.6
FIG.7
FIG.8

SURGICAL METHOD AND APPARATUS FOR FUSING ADJACENT BONE STRUCTURES

CROSS-REFERENCE TO RELATED APPLICATION

This is a division and continuation-in-part of our Ser. No. 259,031, filed Oct. 17, 1988, U.S. Pat. No. 4,961,760 issued on Oct. 9, 1990.

BACKGROUND OF THE INVENTION

1. Field of the Invention

The invention concerns method and apparatus for fusing two adjacent bony structures such as a bone joint, especially adjacent vertebrae of the spine.

2. Description of Related Art

Subsequent to injury, disease or other degenerative disorder, the disc, a ligamentous cushion between vertebrae, may undergo a painful deterioration. The disc shrinks and flattens out, and the distance between the vertebral bodies begins to collapse. Subsequently, there may be a progressive degeneration leading to mechanical instability, where painful translocations occur between adjacent vertebrae. The movement-induced pain, may be so disabling that in many such cases, the vertebral motion must be eliminated. Thus, rigid fusions may be the only present means to stop the translocations and relieve the pain.

It is generally held that successful fusions demand a contiguous growth of bone to create a solid mass that will unite the movable elements into one unit. Otherwise, the fusion cannot achieve the tasks of pain reduction maintenance of intervertebral height, and immobility of the vertebrae. When fusion bone is first placed, it is soft and movable, having no cohesive strength. Therefore a variety of appliances have been developed that attempt to hold the vertebrae quite still under conditions of normal spinal activity and daily stress. Bone graft material is placed between the vertebrae, the outer or cortical surfaces of which have been removed or deeply scarified so as to promote the ingrowth of the graft into these recipient sites. Thus positioned, the bone graft slowly unites the vertebrae. Such an appliance is not meant to permanently secure immobility of the segments Bone ingrowth is required for this.

Dependency upon such an appliance as the sole stabilizer is ultimately unsuccessful due to the development of a mechanical gap or transition between the bone and the appliance, leading to structural failure of the bone and adjacent connective tissue. Such failure is seen in fractures, erosion and absorption of bone with potential further collapse The pain may also become progressively disabling.

Approximately 150,000 lumbar spinal fusions were performed in the USA during 1987, as reported by the American Hospital Association. There are many methods for intervertebral fusion. The most successful have achieved a success rate of about 90% in random cases. However, several of these techniques, especially those requiring complex appliances, are difficult to master and are hazardous to nerve and vessel structures normally lying close to the involved bones.

From a biomechanical point of view, the most important location of a spinal fusion is at the mechanical center of rotation between the vertebrae. This point is centered within the disc space. Therefore, an interbody fusion is the most rigid and thus the most sought after method among surgeons. Current methods of interbody fusions are, however, the most hazardous of all spinal fusion methods.

Both anterior (transabdominal) and posterior surgical approaches are used for interbody fusions. Typically, a plug, dowel or segment of bone is driven tightly into a cavity carved inside the interbody, intradiscal space. Since there must be a bone-to-bone bridge created during the fusion process, connective tissue and discal tissue must be removed. Deep cuts within the bone must penetrate into the softer, cancellous region to promote bone growth across the space.

Intervertebral fusions using circular bone grafts have been reported in the orthopedic and neurosurgical literature for some years. B. R. Wiltberger in a paper published in Clinical Orthopedics, Vol 35, pp 69-79, 1964, reviewed various methods of intervertebral body fusion using posterior bone dowels driven firmly into a suitably smaller hole between the adjacent vertebrae. Upon doing so the dowel can split or crack or collapse. The stretched bone might also split and it can be compressed by the dowel to the point that it will not grow normally due to collapse of formerly open pores or vascular channels. If this occurs, there may be a late absorption of surrounding bone and the dowel might loosen, with a renewed danger of expulsion. See also a 2-page brochure from Neurological Surgery Associates of Cincinnati, Inc. entitled "Posterior Lumbar Interbody Fusion Made Simple" which shows, after the bone dowel placement, the "(a)pplication of 5 mm dacron suture around spinous processes."

U.S. Pat. No. 4,501,269 (Bagby) describes a surgical procedure for stabilizing the cervical spine of a horse and says that the procedure:

> "is applicable to any human or animal joint formed by opposed contiguous bony surfaces which are covered and separated by intervening cartilage and are surrounded by ligaments which resist expansion of the joint. Specific examples of such joints are a spinal joint between adjacent vertebrae or the ankle joint. The process was developed to immediately stabilize the joint and to further promote ultimate bone-to-bone fusion. . . The implanted structure is in the form of a perforated cylindrical bone basket which can be filled with bone fragments produced during the preparation of the joint. These bone fragments provide autogenous tissue to promote bone growth through the basket, as well as around it.
> 
> "The process involves the initial steps of surgically accessing the joint and removing intervening cartilage located between the contiguous bony surfaces. A transverse cylindrical opening is then bored across the contiguous bony surfaces. Immediate stabilization is achieved by driving into the cylindrical opening a hollow basket having a rigid perforated cylindrical wall whose outside diameter is slightly greater than the inside diameter of the cylindrical opening. The implanting of the basket spreads the bony surfaces apart in opposition to the resistance to expansion of the joint provided by the surrounding ligaments" (col. 2, lines 26-55).

U.S. Pat. No. 2,537,070 (Longfellow) shows in FIG. 2 a "reinforce 7" that is much like Bagby's fusion basket.

Vich, J. Neurosurg., Vol 63, pp 750-753 (1983) describes a means for cervical spine fusion, using an anterior approach, by surgically implanting a cylindrical bone graft.

"Screw threads are placed in the graft with a small, previously sterilized die. The grooves of the thread can be made as deep as required. The vertebral cervical bodies are prepared according to Cloward's technique. After a cylindrical bed has been drilled in the appropriate intervertebral bodies, the graft is screwed into place with instruments especially developed for this purpose" (p. 750).

Vich's FIG. 2 legend points out that a threaded graft dowel has a larger contact surface than a plain dowel and a greater resistance to pressure and sliding. Vich also says:

"When grafts with a diameter of 14 mm were used, we sometimes threaded the receiving bed with a die-stock of 13 mm to facilitate the insertion" (p. 751).

An additional desirable effect of an intervertebral fusion is the restoration or maintenance of a normal intervertebral spacing. Spreading devices are generally required in order to restore all or a part of the normal intradiscal height, in the process of placing the fusion material or appliance. When the procedure is performed using the commonly employed posterior approach, a variety of spreaders may be placed between various posterior bony elements normally attached to the vertebrae, such as, dorsal spinous processes or laminas. Using such spreaders, a forward tilt or wedging of the discal space occurs, with the posterior aspect of the space becoming more open than the anterior. When a bone graft of any shape is driven into a cavity that is wedged more open posteriorly between two opposing movable vertebrae, there is a strong propensity for the graft to be retropulsed during the postoperative recovery period as a result of to and from movement between the opposing vertebrae. Thus, to aid in the prevention of graft expulsion, it would be desirable to have the cavity either maintain parallelism or be slightly narrower at its most posterior portion. Ventral to this cavity, the stout ligamentous disc annulus remains and prevents ventral migration of the graft into the retroperitoneal space. Further, there is value in restoring the original spinal lordotic curve, as the fusion grows; this requires that the cavity and the interbody fusion element be placed to promote a normal spinal anatomical position, that is, without wedging of the space in either direction.

In U.S. Pat. No. 4,743,256 (Brantigan) pairs of plugs are implanted as struts spanning and maintaining the disc space between adjacent vertebrae. While bone plugs were previously used in the same way, Brantigan employs "rigid plugs of structural material having porous surfaces to facilitate ingrowth of bone tissue" (col. 2, lines 66-68), inserting these into "grooves bridging the cancellous bone of one vertebral body to the cancellous bone of the subjacent vertebral body..." (col. 2, lines 1-6). "The plugs are preferably made of an inert metal substrate such as stainless steel ... having a porous coating of metal particles ..." (col. 3, lines 8-14). The plug of FIG. 12 "has bone piercing tangs or points 31" (col. 5, line 61).

SUMMARY OF THE INVENTION

The present invention provides a method for implanting a fusion cage in order to fuse adjacent bony structures, which method is safer, surer, easier and faster as compared to the implantation of bone dowels or Brantigan's rigid plug or Bagby's fusion basket or Longfellow's "reinforce." Briefly, the novel implantation method involves the following steps:
 (a) forming between said bony structures a lateral bore with a female thread that penetrates into their cancellous regions,
 (b) forming a hollow cylindrical fusion cage to have an external, substantially continuous helical thread (preferably a V-thread) that is perforated in the valley between adjacent turns and can mate with said female thread,
 (c) screwing the cage into said threaded bore, and
 (d) packing the cage with bone-inducing substance.

The female thread formed in step (a) preferably is tapped by hand, using a slow motion to ensure against burning the bone. This freshens the bone margins of the bore so that if any bone had been burned by drilling to form the bore, it is now cut away slowly by hand. The tapping process is quite safe, in that the surgeon can feel the progress of the technique.

The V-thread or other male-thread fusion cage preferably is screwed by hand into the threaded bore, again permitting the surgeon to feel if the resistance is too great and that rethreading of the bore might be required. In contrast, a bone dowel typically is driven into a bore using a hammer, and in order to guard against an overly tight fit, the surgeon listens to the sound of the striking hammer and also monitors the degree of resistance.

Parent U.S. Pat. No. 4,961,740 indicates that the V-thread fusion cage preferably is made of implantable-grade stainless steel and that titanium is also useful. Currently, titanium is preferred, it having been shown to be more compatible to bone.

Parent U.S. Pat. No. 4,961,740 also teaches that the V-thread fusion cage preferably is fitted with end caps. The end caps preferably are X-ray transparent to permit post-operative checks on the status of the developing bone. X-ray transparent end caps can be stamped from a flexible sheet of thermoplastic resin such as "Delrin" acetal resin or polypropylene and may have a small opening for an instrument by which they can be put into place.

A threaded bore into which a hollow cylindrical fusion cage can be surgically implanted to fuse adjacent bony structures can be prepared by the steps of:
 (a) drilling a pilot hole laterally between said bone structures,
 (b) inserting a pilot rod into the pilot hole,
 (c) fitting a hollow drill over the pilot rod,
 (d) with the hollow drill, enlarging the pilot hole to form a bore that penetrates into the cortical bone of each of said bony structures, and
 (e) tapping a female thread into the wall of said bore with the crown of the thread penetrating into the cancellous portion of each of said bony structures.

When using a male-thread fusion cage between adjacent vertebrae to promote bone ingrowth, the fusion cage should be implanted in pairs on opposite sides of the disc space. After placement of the first cage, there is an impressive, instant stabilization of the previously unstable vertebral segment. The second cage is then screwed into its tapped hole, thus rendering the space completely immobile. Each cage is held in place by its male-thread, biting into female threads that were formed in step (e). Gravity, muscle pull and elastic recoil of the spread (or stretched) outer disc annulus together exert force against each of the fusion cages. Thus the fusion cages are held in place by compression forces between the adjacent vertebrae.

Because the cancellous bone of the vertebral bodies has internal strength similar to wet balsa wood and a hard shell similar to about a 1.5 mm veneer of white oak, it is difficult to drill parallel bores without the drill bits wandering into a common center, unless a drill guide or jig is provided. This problem is met by the following method of forming and threading a bore between adjacent vertebrae, which method involves the following steps:

(a) cutting away ligaments to expose the site,
(b) spreading the vertebrae apart,
(c) nibbling away as much of each lamina as is necessary to access the site,
(d) drilling a pilot hole laterally between said vertebrae, each of sufficiently small diameter to be self-seeking of the center of the disc space,
(e) inserting a pilot rod into the pilot hole,
(f) sliding over the pilot rod a hollow lamina drill to cut the spinous process and to score the lamina,
(g) drilling to remove the lamina within the score,
(h) fitting into the resulting arcuate opening in the lamina a C-retractor which has a split cylindrical sleeve of the same diameter as the lamina drill, a handle extending from one end toward the upper end of the spine, and spikes at its other end,
(i) forcing at least one of the spikes into each of said adjacent vertebrae to anchor the C-retractor,
(j) reinserting the pilot rod to rest on the bottom of the pilot hole,
(k) sliding a hollow vertebral drill over the pilot rod and inside the sleeve of the C-retractor,
(l) forming with the hollow drill a bore that penetrates into the cortical bone of each of said vertebrae,
(m) removing the hollow drill, the pilot rod, and the cut bone, and
(n) using the C-retractor as a guide, tapping a female thread, the crown of which extends into the cancellous bone of each of the vertebrae.

As indicated in the drawing, said pilot rod and the shafts of said hollow lamina drill and tap have markings to show the depths to which they penetrate into the bore.

When male-thread fusion cages are to be positioned between adjacent vertebrae, the sides that are to face laterally preferably are closed to prevent disc tissue from growing into the cages, because this could interfere with bone growth between the vertebrae. By leaving the lateral sides closed, the fusion cages have greater structural strength, thus permitting the perforations adjacent the vertebrae to be larger. When leaving the lateral quadrants closed, we have achieved 70% perforation of the area of the top and bottom quadrants (as projected onto the inner face of a cylinder) while maintaining good compressive strength.

End caps can help to prevent disc tissue from growing into the cages, and for this reason, any openings in the end caps should be small.

A large majority of patients requiring intervertebral fusions have narrowing of the disc space, typically 10 mm or less in the lower back. Because minimal penetration into the end plates of the vertebrae is required (about 3 mm for each), three major diameters of the fusion cage thread should suffice for most patients, namely, 14, 16 and 18 mm. Because the anterior-posterior dimension of a typical lower lumbar vertebra is about 30 mm, the length of the fusion cage preferably does not exceed 25 mm but is at least 20 mm in length to give sufficient contact as well as a good platform when implanted in pairs.

A novel interbody spreader in the form of a scissors jack has been developed to maintain a desirable parallel attitude between the adjacent vertebrae while the bore is drilled and then tapped by a novel instrument.

Other instruments that have been developed for use in the implantation of the novel fusion cage include tapping instruments for forming helical threads in a bore in recipient bone. A first novel tapping instrument comprises a hollow cylindrical shaft having a handle at one end and an external thread which is formed at the other end with at least one scallop that exposes a cutting edge, and a pilot rod that slidably fits into said bore, projects beyond said other end of the hollow shaft, and is formed with a central recess that communicates with the scallop in the hollow shaft and provides a reservoir for detritus removed by said cutting edge, thus permitting the detritus to be carried away by removing the pilot rod from the hollow shaft. The portion of the pilot rod that projects beyond said other end of the hollow shaft preferably is threaded to carry detritus upwardly to the reservoir.

When using this first novel tapping instrument to form female threads for an interbody fusion, the hollow shaft should have an odd number of scallops and cutting edges, preferably three, because an odd number provides more equal removal of recipient bone on both sides of the bore than would an even number.

Said first novel tapping instrument and a novel wrench are illustrated in the drawing, together with other instruments that can be used to implant male-thread fusion cages surgically.

THE DRAWING

In the drawing, all figures of which are schematic,

FIG. 1 is an exploded isometric view of a first V-thread fusion cage of the parent U.S. Pat. No. 4,961,740 and two perforated end caps;

FIG. 2 is an isometric view illustrating the formation of a body that can be cut to form a series of second V-thread fusion cages of said U.S. Pat. No. 4,961,740;

Figure 9:
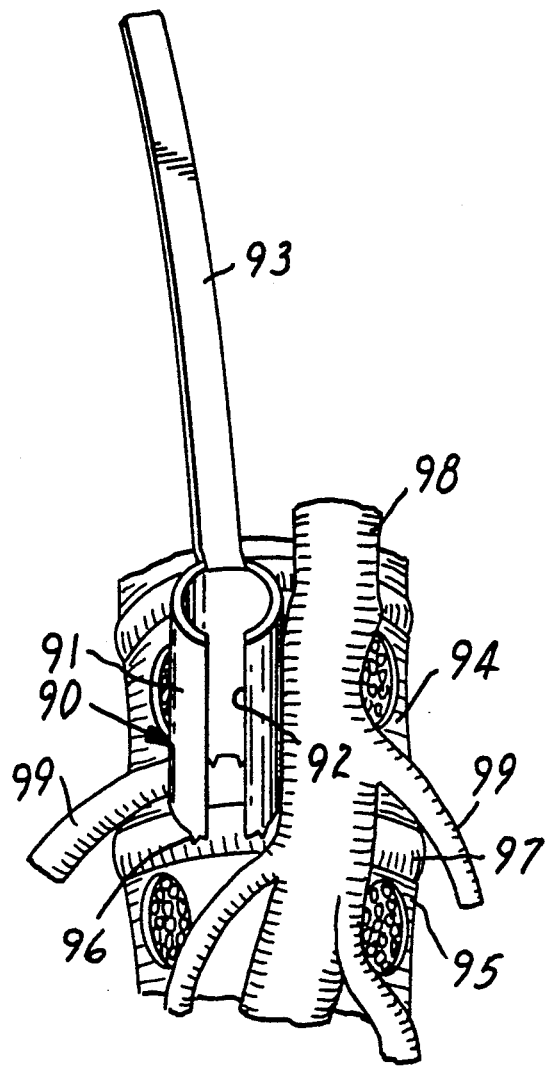
Figure 10:
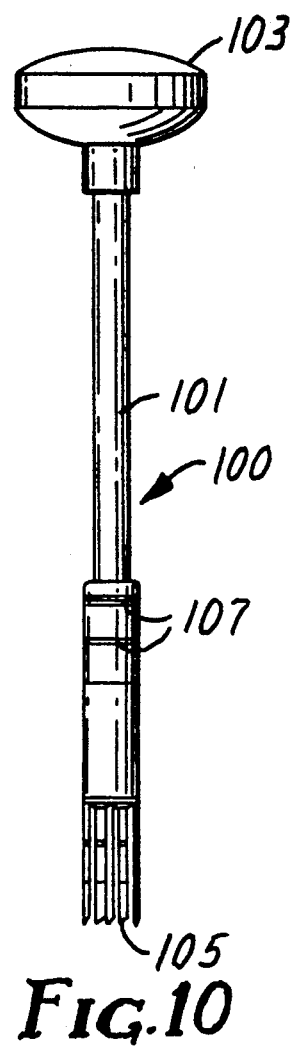
Figure 11:
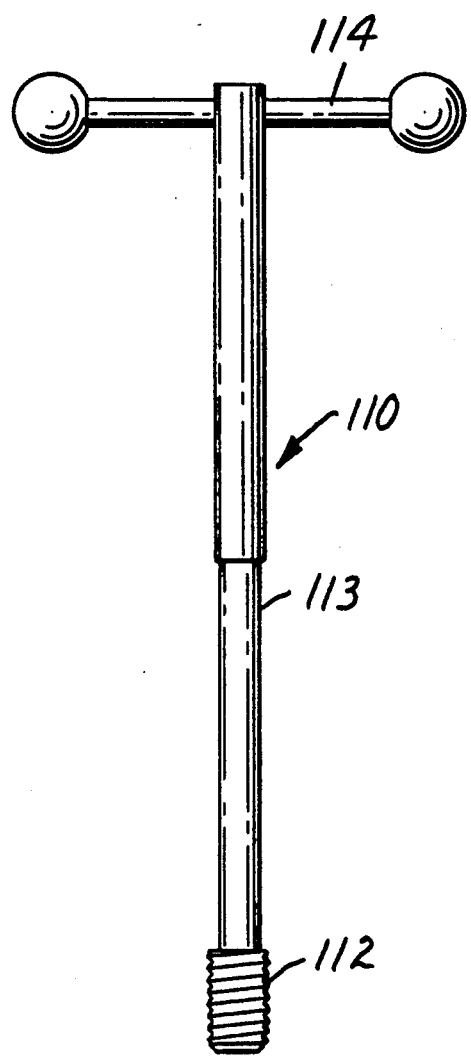

FIG. 5 is an exploded isometric view of a third male-thread fusion cage of said U.S. Pat. No. 4,961,740;

FIG. 6 is a plan view of a pilot drill that can be used in preparation for forming a threaded bore laterally between two vertebrae into which a male-thread fusion cage can be surgically implanted;

FIG. 7 is a plan view of a pilot rod that also can be used in preparation for forming said threaded bore;

FIG. 8 is a plan view of a hollow lamina drill that can be used in conjunction with the pilot rod of FIG. 7;

FIG. 9 is an isometric view showing the use of a C-retractor in preparation for the surgical implantation of a pair of male-thread fusion cages between two vertebrae;

EIG. 10 is a plan view of a hollow vertebral drill that also can be used with the pilot rod of FIG. 7; and FIG. 11 is a plan view of a second tapping instrument that can be used in conjunction with the C-retractor of FIG. 9 to tap a female thread in the bore formed by the hollow vertebral drill of FIG. 10.

DETAILED DESCRIPTION OF THE PREFERRED EMBODIMENT

Figure 1:
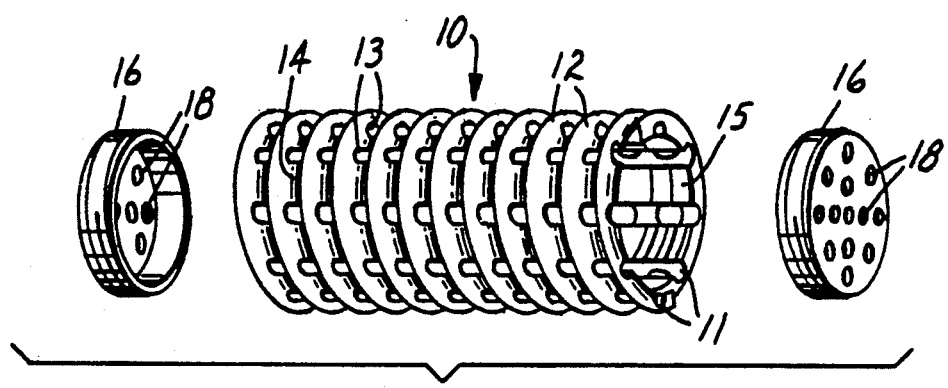

The fusion cage 10 of FIG. 1 was formed from a solid steel cylinder by drilling eight small, equally spaced holes 11 in the axial direction, each hole being centered on a circle concentric with the axis of the cylinder. Then a large hole was drilled centered on the axis and having a radius substantially identical to that of the aforementioned circle. A V-thread 12 was then machined in the external surface of the cylinder, thus opening through that surface a perforation 13 extending through the rounded valley 14 of the V-thread at each crossing of the valley and one of the small holes 11. A screw thread 15 was then machined in the internal surface of the fusion cage to threadably receive an end cap 16 that has apertures 18 similar to those of a salt shaker. Snap-on end caps would also be useful.

In making a fusion cage by the technique described in the preceding paragraph, the small holes 11 could be enlarged to intersect each other, thus making it unnecessary to drill a central hole. Enlarged small holes would result in larger perforations 13.

Figure 2:
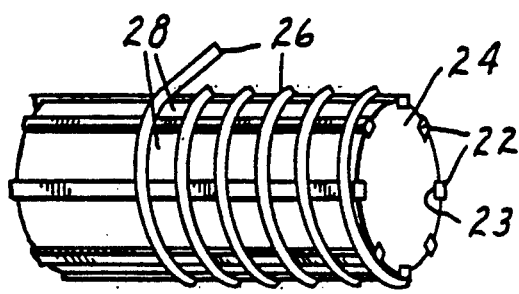

Referring to FIG. 2, a series of fusion cages can be made from a plurality of rods 22 of rectangular cross-section that can be continuously extruded and fed into each of eight keyways 23 in the surface of a mandrel 24. Simultaneously, a rod 26 of triangular cross-section is extruded, wrapped helically around the rectangular rods 22, and soldered or welded to each of the rectangular rods 22 at every crossing to provide an external V-thread. Upon emerging from the keyways, the resulting body is cut into individual fusion cages each of which has a perforation 28 between adjacent turns of the V-thread-forming rod 26 wherever it bridges a gap between adjacent rectangular rods 22.

A fusion cage identical to that of FIG. 2 can be made from a hollow cylinder by machining an external V-thread and broaching a plurality of rectangular internal keyways.

Each of the fusion cages of FIGS. 1 and 2 could be made from a model by the lost wax process.

Figure 3:
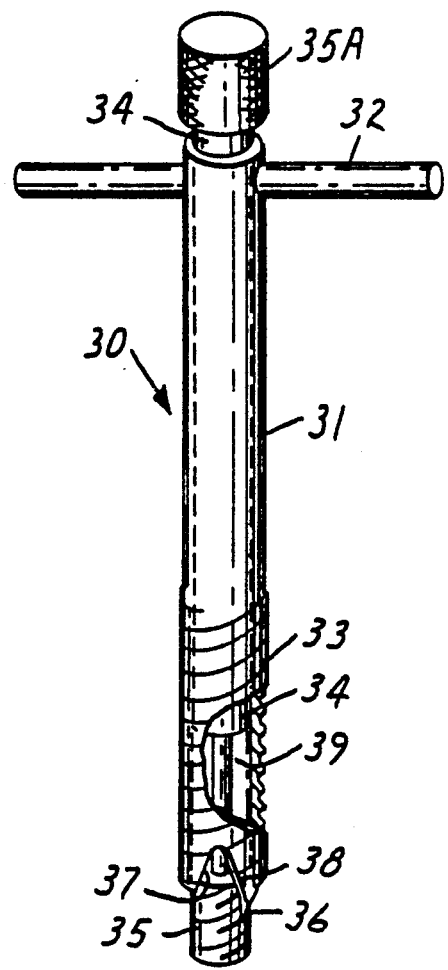
FIG. 3 is an isometric view of a first- tapping instrument (partly cut away to reveal details of construction) for forming female threads in bores into which a male-thread fusion cage is to be inserted.

The tapping instrument 30 of FIG. 3 has a hollow cylindrical shaft 31 with a T-handle 32 at one end and an external thread 33 at the other end. Slidably received within the hollow shaft is a pilot rod 34, one end 35 of which protrudes beyond the hollow shaft 31 and slidably fits into a bore that has been drilled into the recipient bone. At the other end of the pilot rod is a knurled cap 35A. Projecting from the threaded end of the hollow shaft 31 are cutting teeth 36 that enlarge the bore to the minor diameter of the external thread 33 of the hollow shaft 31. The threaded end of the hollow shaft also is formed with three symmetrical scallops 37 (one shown) to expose a cutting edge 38 at the leading edge of the external thread 33, which cutting edge forms female bone threads in the bore upon rotation of the hollow shaft.

Detritus created by tapping instrument 30 is deposited through the scallops 37 into a reservoir provided by a central recess 39 in the pilot rod 34. The end 35 of the pilot rod which extends from the recess 39 into the bore has external threads which, when the threaded pilot rod 34 is turned, carry detritus upwardly to be deposited through the scallops into the reservoir.

Upon rotating the hollow shaft 31 to form female bone threads in the bore, the surgeon can feel increased back pressure when the reservoir becomes full and should grasp the knurled cap 35A to remove and clean out the pilot rod. If the gummy nature of the detritus were to prevent the pilot rod from being easily pulled out of the hollow shaft, the knurled cap 35A could be removed to permit the hollow shaft 31 to be unscrewed from the threaded bore, leaving the pilot rod in place. The pilot rod then serves as a guide if the bore has not yet been completely tapped and it is necessary to reinsert the hollow shaft to complete the tapping.

Figure 4:
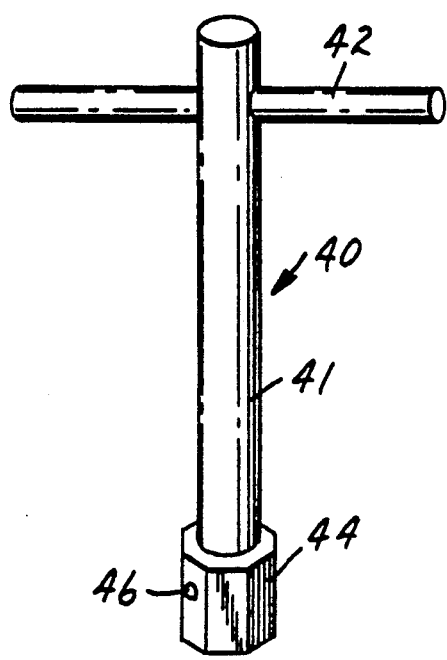
FIG. 4 is an isometric view of a wrench for screwing a male-thread fusion cage into a threaded bore.

The wrench 40 of FIG. 4 has a cylindrical shaft 41 with a T-handle 42 at one end and an octagonal protuberance 44 at the other end. The corners of the protuberance 44 fit into recesses in the fusion cage to permit the fusion cage to be rotated by rotating the wrench. A spring-loaded ball 46 frictionally holds the protuberance in place when it is inserted into the fusion cage.

FIG. 5 shows a third male-thread fusion cage 50 that has formed from a solid steel cylinder by drilling an axial bore 51 and then broaching out a pair of cylindrical channels 52 that extend to a diameter only a little smaller than the external surface of said cylinder. A V-thread 53 has then been machined in that external surface, thus creating perforations 54 in the valley between adjacent turns of the thread, each perforation extending completely across one of the channels 52. Each end of each land between the channels has been machined to have a recess 56 to enable an end cap 57 to fit flush with the end of the fusion cage. At each recess 56, each land has been formed with a small bore 58 into which one of a pair of projections 59 from the end cap 57 fits snugly to hold the end cap in place.

In FIG. 6, a pilot drill 60 has a T-handle 62 at one end of a shaft 63 and at the other end a collar 64 holding a bit 66. A set screw 68 in the collar permits the protruding length of the bit to be adjusted, and the larger diameter of the collar acts as a stop. Typically, the bit 66 extends 25 mm beyond the collar 64.

In FIG. 7, a pilot rod 70 has a cylindrical shaft 71, at one end of which is a cylindrical boss 72 that is 30 mm in length and slidably fits into a bore formed by the pilot drill 110 of FIG. 11. The boss 72 has two scribe marks 73 that indicate the depth in cm of the bore. At its other end, the shaft 71 is formed with a flat 75 that has scribe marks 76 marked to indicate 0, 1, 2 and 3 cm for purposes explained below.

Shown in FIG. 8 is a hollow lamina drill 80 which has a cutting edge 82 and a central bore 83 that slidably fits over the shaft 71 of the pilot rod 70. An anodized aluminum handle handle 84 permits a surgeon to drive the lamina drill by hand.

Shown in FIG. 9 is a C-retractor 90 which has a cylindrical sleeve 91 that is formed with an opening 92 across about one-fourth of its circumference over its full length. Extending from one end of the sleeve opposite to said opening 92 is a malleable handle 93 by which the cylindrical sleeve 91 can be fitted through the arcuate laminotomy (formed by the lamina drill 80) down to the vertebrae 94 and 95. At the other end of the sleeve 91 are four spikes 96 in two pairs, one pair on either side of a line that is 180° from the center of said opening 92. When the sleeve of the C-retractor 90 is concentric with a pilot bore that has been drilled laterally into the disc 97 between the two vertebrae 94 and 95, one pair of the spikes can be set into the dorsal surfaces of each vertebra after careful orientation to be concentric with the pilot rod 70 while it is seated in the pilot bore. As also shown in FIG. 9, one purpose of the sleeve 91 of the C-retractor 90 is to keep tools from contacting the dura 98 and the spinal nerve 99.

Shown in FIG. 10 is a hollow vertebral drill 100, the shaft 101 of which is formed with a central bore (not shown) that slidably fits over the shaft 71 of the pilot rod 70 while the C-retractor 90 is in place. At one end of the hollow drill are scalloped cutting edges 105, and at the other is a hard rubber handle 103 that permits a surgeon to drive the vertebral drill by hand. Scribe marks 107 indicate 0, 1, 2 and 3 cm. The 0 mark is at the top of the cylindrical sleeve 91 of the C-retractor when the vertebral drill is first put into place, and it and the other marks sequentially disappear behind the cylindrical sleeve as the vertebral drilling progresses. At the same time the scribe marks 76 on the flat 75 of the shaft 71 of the pilot rod 70 appear behind the handle 103 of the vertebral drill. While the surgeon watches the disappearance of the scribe marks 107 on the vertebral drill, a surgical assistant holds the pilot rod at the proper attitude and monitors the progress of the drilling by watching the appearance of the scribe marks 76 on the pilot rod. The greater inside diameter of the C-retractor 90 compared to that of the scalloped cutting edges 105 affords to the surgeon the opportunity to make slight lateral corrections as the drilling progresses.

Shown in FIG. 11 is a second tapping instrument 110, the tap 112 of which slidably fits into the cylindrical sleeve 91 of the C-retractor 90. At the other end of its shaft 113 is a T-handle 114 by which a surgeon drives the tap until it reaches the depth of the bore.

Implanting the Fusion Cage of FIG. 1

In order to implant the fusion cage 10 between adjacent vertebrae, soft, collagenous disc material is first removed from the intervertebral space. A small window is created in the overlying laminas of each side, namely, standard laminotomies. The neural tissues, dural sac and nerves, are retracted medially. The intervertebral space is cleaned of disc material in a standard surgical fashion. If the disc space has narrowed as a result of degeneration, a scissors-jack type vertebral spreader or a hydraulically inflated bladder is inserted on one (the first) side inside the disc space and opened until the space approximates the normal. This may be confirmed by a lateral x-ray. The height of the disc space is measured on the x-ray so that the proper sizes of drills, tap, and fusion cage may be chosen.

The opposite (second) side of the same disc space is then addressed. The nerve tissues on the first side are relaxed and then retracted medialward on the second side. A pilot drill (e.g., 5 mm or 8 mm diameter depending upon discal space height) cuts a small channel in the face of each of the vertebrae, penetrating the interdiscal space to a depth of about 25 mm (the normal disc space is about 30 mm deep and 50 mm wide). A drill stop may be applied to the drill to prevent overboring the hole. A solid rod pilot is then inserted into the pilot hole and a pilot cutter (7 mm or 10 mm) is passed over it and brought downward to enlarge the pilot channels to slidably receive the pilot rod 35 of the tapping instrument 30 of FIG. 3. The cutting thread 33 (12 mm or 16 mm major diameter) cuts female bone threads through the opposing vertebral end plates and into both cancellous regions that will invite the ingrowth of new bone.

A V-thread fusion cage of the invention, with one end cap in place, is snapped onto the wrench 40 of FIG. 4 by which it is screwed by hand into the threaded intradiscal bore to its full depth. After removing the wrench, the cage is packed with bone chips or other bone-inducing substance, and the second end cap is applied to hold the bone chips securely in place.

After removing the vertebral spreader, the dura and nerves on the second side are relaxed and attention is once again directed to the first side which is drilled and tapped to receive a second fusion cage by the same procedure.

Over a period of several weeks, the bone from the vertebral bodies will grow through the perforations in the fusion cages and unite with the bone-inducing substance inside them, creating a solid fusion.

It is believed that the novel fusion cages will primarily be implanted by a posterior approach to the spine, although an anterior approach may be utilized, especially when applied to the cervical spine.

EXAMPLE 1

The fusion cage of FIG. 1 has been machined from a cylinder of surgically implantable stainless steel to have the following dimensions:

| | |
|---|---|
| diameter of starting cylinder | 16 mm |
| length of cylinder | 25 mm |
| diameter of each small hole 11 | 3 mm |
| diameter of circle on which holes 11 are centered | 11.5 mm |
| diameter of central hole | 11 mm |
| pitch of V-thread 12 | 2.5 mm/turn |
| angle at crown of thread 12 | 60° |
| fillet radius in valley of thread 12 | 0.4 mm |
| axial width of perforations 13 | 1.6 mm |
| circumferential breadth of perfs. 13 | 2.8 mm |
| when projected onto interior of a cylinder, % of area perforated | 25% |

EXAMPLE 2

The fusion cage of FIG. 1 has been machined from a stainless-steel cylinder to have the same dimensions as that of Example 1 except that the diameter of the circle on which holes 11 were centered was increased to 12 mm. This resulted in 70% perforation in each of the areas of the top and bottom quadrants.

To test the compressive strength, a pine block was drilled to the outside diameter of the thread of the fusion cage, and a ¼-inch section was cut away to leave two pieces, between which the fusion cage was placed with its perforations facing the two pieces. A force of 808 pounds was applied before the fusion cage began to deform into an oval shape, thus indicating that it has much more than adequate compressive strength to withstand any forces to which it might be put when implanted between a person's vertebrae.

EXAMPLE 3

A fusion cage, identical to that of Example 2 except that the cage was made from titanium, was tested in the same way for compressive strength. It resisted 850 pounds before beginning to deform.

Surgical Experience

The fusion cage of Example 2 has been surgically implanted in pairs between adjacent vertebrae of each of three persons. In each case after placement of the first cage, there was an impressive, instant stabilization of the previously unstable vertebral segment. Upon threading the second cage into its tapped hole, the segment became completely immobile.

Each of those three patients was able to tolerate sitting without low back pain by the second or third post-surgical day. This unexpectedly early comfort expressed by each of these three patients signified good, immediate stability to the previously painfully unstable spinal segment.

The first patient, on a routine visit at two months postoperative, had an almost full range of painless motion (bending, twisting) of the lumbar spine. The second patient, at 18 days postoperative, made an unscheduled visit to ask permission to go biking and reported a greater than 90% relief of all back and leg pains. The third patient showed approximately ⅔ range of normal painless motion of the lumbar spine on the sixth postoperative day.

What is claimed is:

1. Surgical method of fusing adjacent vertebral bony structures, said method comprising the steps of
   (a) spreading apart the adjacent vertebral bony structures, and forming between said vertebral bony structures a lateral bore, which extends into the disc space between adjacent vertebral bony structures, with a female threat that penetrates into cancellous regions of the bony structures,
   (b) selecting an appropriately sized hollow cylindrical fusion cage which has an external, substantially continuous helical threat which defines a plurality of turns with a valley between adjacent turns and that is perforated in the valley between adjacent turns and that can mate with said female thread,
   (c) screwing the cage into said threaded bore, and
   (d) packing the cage with bone-inducing substance.

2. Method as defined in claim 1 wherein said threaded bore extends into the disc space between adjacent vertebrae, and prior to step (a) is the added step of spreading said vertebrae apart.

3. Method as defined in claim 1 wherein a second threaded bore is formed to extend into the opposite side of said disc space and parallel to said threaded bore, and steps (b), (c) and (d) are repeated to implant an identical fusion cage in said second threaded bore.

4. Method for surgically preparing two adjacent bony structures for implanting a hollow cylindrical fusion cage that has an external, substantially continuous helical thread which defines a plurality of turns with a valley between adjacent turns and that is perforated in the valley between adjacent turns of the thread, said method comprising the steps of:
   (a) drilling a pilot hole laterally between said bony structures,
   (b) inserting a pilot rod into the pilot hole,
   (c) fitting a hollow drill over the pilot rod,
   (d) with the hollow drill, enlarging said pilot hole to form a bore that penetrates into the cortical bone of each of said bony structures, and
   (e) tapping a female thread into the wall of said bore, the crown of which female thread penetrates into the cancellous portion of each of said bony structures, which female thread can mate with the helical thread of the fusion cage.

5. Method as defined in claim 4 wherein said bore extends laterally into the disc space between adjacent vertebrae.

6. Method as defined in claim 5 wherein steps (a) through (e) are repeated to form a second threaded bore parallel to the first, one on each side of the disc space.

7. Method as defined in claim 6 wherein each said female thread is formed in step (e) by hand tapping.

8. Method as defined in claim 4 and further comprising subsequent to step (e) the steps of:
   (f) screwing the fusion cage into said threaded bore, and
   (g) then filling the cage with bone-inducing substance.

9. Method as defined in claim 8 wherein the bone-inducing substance is cancellous bone chips.

10. Method for surgically preparing two adjacent vertebrae for implanting a hollow cylindrical fusion cage that has an external, substantially continuous helical thread which defines a plurality of turns with a valley between adjacent turns and that is perforated in the valley between adjacent turns of the thread, said method comprising the steps of:
    (a) cutting away ligaments to expose the site,
    (b) spreading the vertebrae apart,
    (c) nibbling away as much of the lamina as is necessary to access the site,
    (d) drilling a pilot hole laterally between said vertebrae of sufficiently small diameter to be self-seeking of the center of the disc space,
    (e) inserting a pilot rod into the pilot hole,
    (f) sliding over the pilot rod a hollow lamina drill to cut the spinous process and to score the lamina,
    (g) drilling to remove the lamina within the score then removing the hollow lamina drill and the pilot rod,
    (h) fitting into the resulting acruate opening in the lamina a C-retractor which has a split cylindrical sleeve of about the same diameter as the lamina drill and a handle extending from one end toward the upper end of the spine,
    (i) reinserting the pilot rod to rest on the bottom of the pilot hole,
    (j) sliding a hollow vertebral drill over the pilot rod and inside the sleeve of the C-retractor,
    (k) forming with the hollow drill a bore that penetrates into at least the cortical bone of each of said vertebrae,
    (l) removing the hollow drill, the pilot rod, and the cut bone, and
    (m) using the C-retractor as a guide, tapping a female thread, the crown of which extends into the cancellous bone of each of the vertebrae.

11. Method as defined in claim 10 and comprising the added step of maneuvering aside the dura and nerve with said split cylindrical sleeve of the C-retractor.

12. Method as defined in claim 11 wherein the C-retractor is formed with spikes extending axially from one end of said cylindrical sleeve, said method comprising the added step of forcing at least one of said spikes into each of said adjacent vertebrae to anchor the C-retractor.

* * * * *